United States Patent [19]

Walker

[11] 4,055,652

[45] Oct. 25, 1977

[54] 1-[β(R-THIO)PHENETHYL]IMIDAZOLES AND DERIVATIVES THEREOF

[75] Inventor: Keith A. M. Walker, Palo Alto, Calif.

[73] Assignee: Syntex (U.S.A.) Inc., Palo Alto, Calif.

[21] Appl. No.: 664,453

[22] Filed: Mar. 8, 1976

Related U.S. Application Data

[63] Continuation-in-part of Ser. No. 593,620, July 7, 1975, abandoned, which is a continuation-in-part of Ser. No. 508,384, Sept. 23, 1974, abandoned.

[51] Int. Cl.$^2$ .................. C07D 233/60; A61K 31/415
[52] U.S. Cl. .................. 424/273 R; 542/413; 542/426; 542/427; 548/341
[58] Field of Search .............. 260/309, 240 A, 240 D, 260/240 J; 424/273

[56] References Cited

U.S. PATENT DOCUMENTS

| 3,658,813 | 4/1972 | Godefroi et al. | 260/309 |
| 3,682,951 | 8/1972 | Kreider | 260/309 |
| 3,717,655 | 2/1973 | Godefroi et al. | 260/309 |
| 3,796,704 | 3/1974 | Metzger et al. | 260/309 |

OTHER PUBLICATIONS

Conant et al. The Chemistry of Organic Compounds revised edition p. 264 N. Y., MacMillan, 1939.

*Primary Examiner*—Natalie Trousof
*Attorney, Agent, or Firm*—Alan M. Krubiner; Natalie Jensen

[57] ABSTRACT

Novel 1-[β-(R-thio)phenethyl]-imidazoles and the corresponding 1-[β-(R-sulfinyl)phenethyl]imidazoles and 1-[β-(R-sulfonyl)phenethyl]imidazoles wherein R is alkyl, alkenyl, aralkenyl, substituted aralkenyl, alkynyl, cycloalkyl, cycloalkyl alkyl, aralkyl, substituted aralkyl, aryl or substituted aryl; and the antimicrobial acid addition salts thereof, are useful as antifungal, anti-bacterial and anti-protozoal agents.

46 Claims, No Drawings

1-[β(R-THIO)PHENETHYL]IMIDAZOLES AND DERIVATIVES THEREOF

RELATED APPLICATIONS

This case is a continuation-in-part of pending U.S. Ser. No. 593,620, filed July 7, 1975, now abandoned which is a continuation-in-part of U.S. Ser. No. 508,384, filed Sept. 23, 1974, now abandoned.

The present invention relates to novel imidazole derivatives and more particularly to 1-[β-(R-thio)-phenethyl] imidazoles, 1-[β-(R-sulfinyl)phenethyl]-imidazoles and 1-[β-(R-sulfonyl)phenethyl]imidazoles having the formula

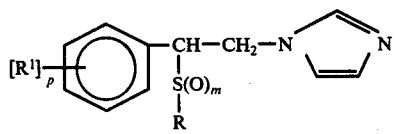
(I)

and the antimicrobial acid addition salts thereof, wherein:

R is alkyl, alkenyl, aralkenyl, substituted aralkenyl, alkynyl, cycloalkyl, cycloalkyl alkyl, aralkyl, substituted aralkyl, aryl or substituted aryl, said substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino, acylamino and cyano;

$R^1$ is hydrogen, halo, lower alkyl, lower alkoxy, trifluoromethyl, nitro, cyano, thiocyano or the group

in which $R^2$ is alkyl, cycloalkyl, aralkyl, substituted aralkyl, aryl or substituted aryl, said substituted aralkyl and said substituted aryl containing at least one substituent on the aryl moiety selected from the group consisting of halo, lower alkyl, lower alkoxy, trifluoromethyl, nitro and cyano;

m, n and p are independently selected from the integers zero, 1 and 2; provided that:

the value of m cannot be greater than the value of n except when $R^1$ is the group

and $R^2$ is aryl or substituted aryl.

The term "alkyl" as used in the specification and appended claims refers to a saturated, unbranched or branched acylic hydrocarbon group containing 1 to 20 carbon atoms inclusive, such as methyl, ethyl, n-propyl, isopropyl, n-butyl, i-butyl, t-butyl, n-pentyl, n-heptyl, n-octyl, n-nonyl, n-dodecyl, n-octadecyl and the like. The term "lower alkyl" refers to an alkyl group as previously defined containing 1 to 6 carbon atoms, inclusive. The term "lower alkoxy" refers to groups of the formula lower alkyl—O— wherein the lower alkyl substituent is as previously defined. The term "cycloalkyl" as used herein refers to a saturated, monocyclic hydrocarbon group having 5 to 8 ring carbon atoms, such as cyclopentyl, cyclohexyl, cycloheptyl and the like. The term "cycloalkyl alkyl" refers to a cycloalkyl group as previously defined attached to an unbranched acyclic hydrocarbon group containing 1 to 3 carbon atoms, such as cyclopentylpropyl, cyclohexylmethyl, cyclohexylethyl, cycloheptylmethyl and the like. The term "alkenyl" refers to an unbranched or branched acyclic hydrocarbon group having carbon-carbon double bond unsaturation and containing 2 to 12 carbon atoms such as allyl, 2-hexenyl, 3-octenyl, 2-octenyl, 2-decenyl and the like. The term "aralkenyl" refers to a hydrocarbon moiety in which the alkenyl portion containing 2 to 4 carbon atoms is attached to a hydrocarbon group consisting of one of more aromatic rings and containing 6 to 10 ring carbon atoms such as 3-phenyl-2-propenyl, 4-phenyl-3-butenyl, styryl, 3-naphthyl-2-propenyl and the like. The term "alkynyl" refers to an unbranched or branched acyclic hydrocarbon group having carbon-carbon triple bond unsaturation and containing 2 to 12 carbon atoms, such as 2-propynyl, 3-hexynyl, 2-octynyl and the like. The term "aryl" refers to a hydrocarbon group consisting of one or more aromatic rings and containing 6 to 10 ring carbon atoms, such as phenyl and naphthyl. The term "aralkyl" refers to a hydrocarbon moiety in which the alkyl portion contains 1 to 4 carbon atoms and the aryl portion is defined as above. Representative examples of aralkyl groups include benzyl, 3-phenylpropyl and the like. The term acylamino, i.e., R—C(O)—NH—, refers to substituents containing up to 12 carbon atoms, wherein R in such substituents is methyl, ethyl, i-propyl, n-butyl, pentyl, octyl and the like. The term "halo" as used herein refers to chloro, fluoro and bromo. The term "antimicrobial acid addition salts" refers to salts of the subjects compounds which possess the desired activity and which are neither biologically nor otherwise undesirable. These salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluensulfonic acid, salicylic acid and the like.

All compounds of Formula (I) possess at least one chiral center, i.e., the carbon atom to which are attached the

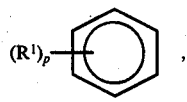, $RS(O)_m$, H and

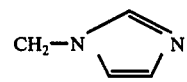

moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subjects compounds.

If desired, racemic intermediates of final products prepared herein may be resolved into their optical antipodes by conventional resolution means known per se, for example, by the separation (e.g., fractional crystallization) of the diastereomeric salts formed by reaction of, e.g., racemic compounds of Formula (I) or the alcohol precursors with an optically active acid, or by separation of the diastereomeric esters formed by reaction of the racemic alcohol precursors of compounds of Formula (I) with an optically active acid. Exemplary of such optically active acids are the optically active forms of camphor-10-sulfonic acid, α-bromo-camphor-π-sulfonic acid, camphoric acid, menthoxy-acetic acid, tartaric acid, malic acid, diacetyltartaric acid, pyrrolidone-5-carboxylic acid, and the like. The separated pure diastereomeric salts or esters may then be cleaved by standard means to afford the respective optical isomers of the compounds of Formula (I) or the precursor alcohols.

A preferred subclass of compounds within the class defined by Formula (I) are those compounds having the formula

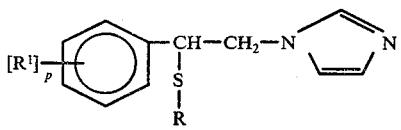

and the antimicrobial acid addition salts thereof, wherein R, R¹ and p are as previously defined.

Preferred compounds within the above defined subclass are those wherein R¹ is halo and R is alkyl, alkenyl, aralkenyl, halo substituted aralkenyl, aralkyl, halo or lower alkoxy substituted aralkyl, aryl or halo or lower alkoxy substituted aryl.

Especially preferred compounds within the group described in the previous paragraph are those wherein R is alkyl containing 1 to 12 carbon atoms, 2-alkenyl, 3-phenyl-2-alkenyl, halo substituted 3-phenyl-2-alkenyl, benzyl, halo or lower alkoxy substituted benzyl, phenyl or halo or lower alkoxy substituted phenyl.

More especially preferred compounds within the group described in the previous paragraph are those wherein [R¹]p is 2,4-dihalo and R is alkyl containing 4 to 10 carbon atoms, halo or methoxy substituted benzyl or halo or methoxy substituted phenyl.

Still more especially preferred compounds within the group described in the previous paragraph are those wherein [R¹]p is 2,4-dichloro and R is a straight chain alkyl containing 4 to 10 carbon atoms, chloro substituted benzyl or chloro substituted phenyl.

Still even more especially preferred compounds within the group described in the previous paragraph are those wherein R is a straight chain alkyl containing 5 to 7 carbon atoms, 4-chloro-, 2,4-dichloro- or 3,4-dichlorobenzyl or 4-chloro-, 2,4-dichloro or 3,4-dichlorophenyl.

Most especially preferred compounds within the group described in the previous paragraph are:
1-[2,4-dichloro-β-(n-heptylthio)phenethyl]imidazole,
1-[2,4-dichloro-β-(4-chlorobenzylthio)phenethyl]-imidazole,
1-[2,4-dichloro-β-(2',4'-dichlorobenzylthio)phenethyl]imidazole and
1-[2,4-dichloro-β-(3',4'-dichlorophenylthio)-phenethyl]imidazole.

The subject compounds of Formula (I) exhibit anti-fungal, anti-bacterial and anti-protozoal activity. For example, compounds of the present invention exhibit anti-fungal activity against human and animal pathogens such as
Microsporum audouini,
Microsporum gypseum,
Microsporum gypseum - canis,
Epidermophyton floccosum,
Trichophyton mentagrophytes,
Trichophyton rubrum,
Trichophyton tonsurans,
Candida albicans, and
Crytococcus neoformans.

The compounds of the present invention also exhibit anti-fungal activity against fungi of primarily agricultural importance such as
Aspergillus flavus,
Cladosporium herbarum,
Fusarium graminearum,
Penicillium notatum,
Aspergillus niger,
Penicillium oxalicum,
Penicillium spinulosum, and
Pithomyces chartarum.

In addition, the compounds of the present invention exhibit anti-bacterial activity against human and animal pathogens, such as
Staphylococcus aureus,
Streptococcus faecalis,
Corynebacterium acnes,
Erysipelothrix insidiosa,
Escherichia coli,
Proteus vulgaris,
Salmonella choleraesuis,
Pasteurella multocida, and
Pseudomonas aeruginosa.

Moreover, the compounds of the present invention exhibit anti-protozoal activity against protozoa such as Trichomonas vaginalis.

In general, the subject compounds of the instant invention are significantly less toxic in small animal tests than the corresponding oxygen analogues, e.g., 1-[2,4-dichloro-β-(4'-chlorobenzylthio)phenethyl]imidazole is less toxic than 1-[2,4-dichloro-β-(4'-chlorobenzyloxy)-phenethyl]imidazole. Moreover, the subject compounds demonstrate good solubility in the stratum corneum. Since dermatophyte (i.e. parasitic fungal) infections are usually localized in the dead tissue of the stratum corneum, solubility of anti-fungal agents in this tissue significantly enhances their effectiveness.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of Formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, composition may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semisolid formulations there may be mentioned, for example, polyalkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials.

In pharmaceutical applications, the subject compounds and compositions may be administered to humans and animals by conventional methods, e.g., topically, orally, parenterally and the like. Parenteral administration includes intramuscular as well as subcutaneous and intravenous injection. Intravenous injection has been demonstrated to be effective in the treatment of systemic mycoses (see for example, Drugs, 9, 419–420 (1975), which described the intravenous administration of miconazole, i.e., 1-[2,4-dichloro-$\beta$-(2',4'-dichlorobenzyloxy)phenethyl]imidazole nitrate, to patients with systemic candidiasis). Topical application is the preferred method of administration in pharmaceutical applications. For such treatment, and area having an existing fungal, bacterial or protozoal growth, or to be protected against attack by fungi, bacteria or protozoa may be treated with the subject compounds or compositions by, for example, dusting, sprinkling, spraying, rinsing, brushing, dipping, smearing, coating, impregnating and the like. Topical pharmaceutical compositions containing the compounds of the present invention exhibit anti-fungal, anti-bacterial and anti-protozoal activity over a wide range of concentration, for example, from about 0.1 to 10.0% by weight of the composition. In any event, the composition to be administered will contain a quantity of the subject compound in an amount effective for relief or prevention of the specific condition being treated.

The pharmaceutical compositions hereof typically comprise one or more subject compounds of Formula (I) and a pharmaceutically acceptable, non-toxic carrier, and are preferably formulated in unit dosage form to facilitate administration (unit dosage being the amount of active ingredient administered on one occasion).

In general, for systemic (e.g. oral or parenteral) administration it is expedient to administer the active ingredient in amounts of between about 1 and 100 mg./kg. body weight per day (preferably between about 5 and 50 mg./kg. body weight per day) distributed over several applications (e.g. in 3 individual doses) in order to achieve effective results. For localized (e.g. topical) administration however, proportionately less of the active ingredient is required. The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgement of the attending practitioner. However, the compositions will in any event contain an effective amount of the active ingredient(s).

In agricultural applications, the subject compounds may be applied directly to plants (e.g., seeds, foliage) or to soil. For example, compounds of the present invention may be applied to seeds along or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known matter. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

DETAILED DESCRIPTION

The present invention, in a still further aspect, is directed to methods for the preparation of the subject compounds of Formula (I) according to the following reaction sequence:

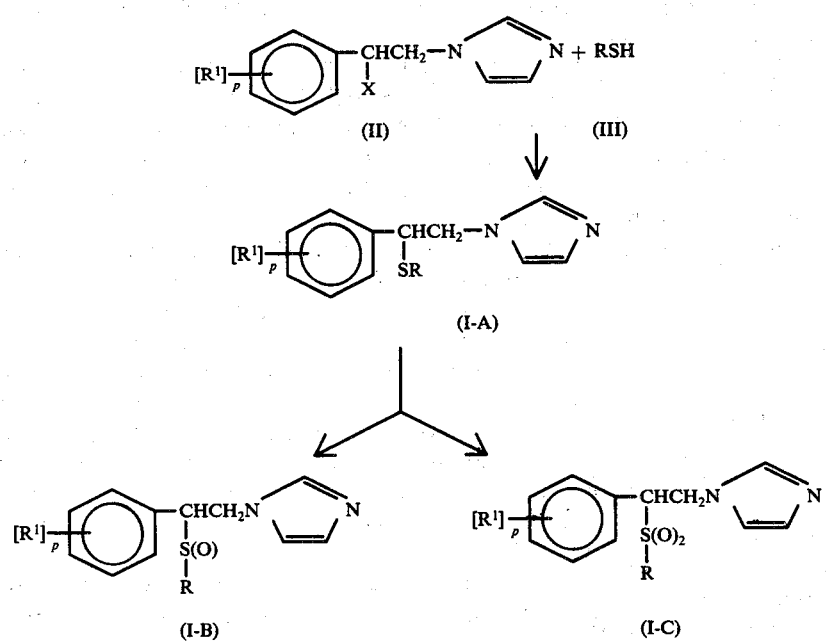

wherein R, R[1] and p are as previously described and X represents chloro, bromo or a reactive ester group such as $CH_3-S(O)_2-O-$ or $p-CH_3-C_6H_4-S(O)_2-O-$.

The 1-[β-(R-thio)phenethyl]imidazoles of Formula I-A are prepared by condensing a 1-(β-substituted phenethyl)imidazole of Formula II with a thiol of Formula III.

The reaction of compounds of Formula II with compounds of Formula III wherein R in Formula III is alkyl, alkenyl, aralkenyl, substituted aralkenyl, alkynyl, cycloalkyl, cycloalkyl alkyl, aralkyl or substituted aralkyl is carried out in the presence of an inert organic solvent, e.g. tetrahydrofuran, ether, methanol and the like in the presence of sodium hydride or other suitable base at a temperature of 20° to 66° C. for a period of 30 minutes to 24 hours.

The reaction of compounds of Formula II with compounds of Formula III wherein R in Formula III is aryl or substituted aryl is carried out in the presence of an inert organic solvent, e.g. acetone, methanol, and the like and in the presence of potassium carbonate or other suitable base under reflux conditions for a period of 30 minutes to 12 hours.

The thus obtained 1-[β-(R-thio)phenethyl]imidazole compounds of Formula I-A are then optionally oxidized to obtain the 1-[β-(R-sulfinyl)phenethyl]- and the 1-[β-(R-sulfonyl)phenethyl]imidazole compounds of Formulas I-B and I-C, respectively. Oxidation is conducted by methods well-known in the art using hydrogen peroxide, an organic peracid such as peracetic acid, p-nitroperbenzoic acid and m-chloroperbenzoic or an inorganic peracid such as periodic acid. The oxidation reaction is preferably conducted using m-chloroperbenzoic in a liquid reaction medium, such as a chlorinated hydrocarbon.

When compounds of Formula I-A are contacted with 1 equivalent of m-chloroperbenzoic acid in chloroform at 0° C. for a period of 30 minutes to 6 hours, the corresponding 1-[β-(R-sulfinyl)phenethyl]imidazole compounds of Formula I-B are obtained.

Alternatively, when compounds of Formula I-A are contacted with 2 to 4 equivalents of m-chloroperbenzoic acid in chloroform at room temperature for a period of 1 to 24 hours, the corresponding 1-[β-(R-sulfonyl)phenethyl]imidazole compounds of Formula I-C are obtained.

The subject compounds of the instant invention can be isolated as free bases, however, since many of the compounds in base form are oils or gums, it is more convenient to isolate and characterize the compounds as acid addition salts. These salts are prepared in the usual manner, i.e., by reaction of the base compound with a suitable inorganic or organic acid, described above. Salts formed with dibasic acids (e.g. oxalic acid) may contain one or two molecules of base per molecule of acid. All oxalates described herein contain one molecule of oxalic acid per molecule of imidazole base. If desired, the salts can be readily converted to the compounds in base form by treatment with alkali, such as potassium carbonate, sodium carbonate or sodium or potassium hydroxide.

The starting compounds of Formula II, wherein R[1] is hydrogen, methyl, methoxy, halo, nitro or lower alkyl sulfonyl are disclosed together with a method for their preparation in U.S. Pat. No. 3,679,697. Compounds of Formula II wherein R[1] is other than those groups disclosed in the above-identified patent, with the exception of R[2]S(O)—, can be analogously prepared, i.e., by bromination of the appropriate acetophenone, reaction of the resultant 2-bromo acetophenone compared with imidazole, reduction of the resultant 2-(1-imidazolyl)acetophenone compound with sodium tetrahydroborate, and finally, reaction of the resultant 1-imidazoleethanol compound with a thionyl halide to yield the 1-(β-halophenethyl)imidazole compounds of Formula II. Compounds of Formula II wherein R[1] is the group R[2]S(O) — are prepared by oxidation of corresponding compounds of Formula II where R[1] is the group R[2]S— using conventional methods known in the art as described earlier in this invention.

When acetophenones containing the group

are required as reactants for the preparation of starting compounds of Formula II, i.e.,

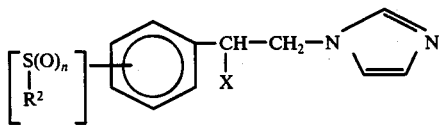

wherein $R^2$, X and $n$ are as previously defined, these acetophenones may be prepared by the following processes:

A. Friedel-Crafts Acylation of a known alkyl-, cycloalkyl-, aralkyl- or aryl phenyl sulfide with acetyl chloride or with acetic anhydride in the presence of $AlCl_3$ to yield the corresponding alkylthio-, cycloalkylthio-, aralkylthio or arylthioacetophenone with can be converted to the corresponding sulfonyl derivatives by oxidation with hydrogen peroxide in acetic acid. These methods are described in the Journal of American Chemical Society 74, 5475-81, (1952) and U.S. Pat. No. 2,763,692.

B. Coupling a diazotized aminoacetophenone with an aryl thiol or a substituted aryl thiol, said substituted thiol containing at least one substituent selected from the group consisting of halo, lower alkyl, lower alkoxy, trifluoromethyl, nitro and cyano, to obtain the substituted arylthio acetophenone. Alternatively, a diazotized aryl amino compound, substituted with at least one of the above substituents can be coupled with a mercaptoacetophenone to obtain the substituted arylthioacetophenone. These procedures are described in Boll. sci. fac. chim. ind. Bologna 17, 33-43 (1959).

C. Alkylation of an o—, m— or p— mercaptoacetophenone with a known alkyl, cycloalkyl, aralkyl or substituted aralkyl halide, said substituted aralkyl halide substituted on the aryl moiety with at least one substituent selected from the group consisting of halo, lower alkyl, lower alkoxy, trifluoromethyl, nitro and cyano to obtain the corresponding alkyl-, cycloalkyl-, aralkyl- or substituted aralkylthioacetophenone. This procedure is described in the Journal of Americal Chemical Society 78, 4792-7 (1956).

Oxidation of the products of processes (B) and (C) in the manner described in process (A) produces the corresponding $R_2$-sulfonylacetophenones wherein $R_2$ is as previously defined.

DESCRIPTION OF SPECIFIC EMBODIMENTS

The following specific description is given to enable those skilled in the art to more clearly understand and practice the present invention. It should not be considered as a limitation upon the scope of the invention but merely as being illustrative and representative thereof.

PREPARATION A

A mixture of 1.52 g. of 4-mercaptoacetophenone, 1.72 g. of 4-methoxybenzyl chloride and 1.5 g. of anhydrous potassium carbonate in 50 ml. of acetone is stirred and refluxed under nitrogen. After 4 hours the solvent and excess 4-methoxybenzyl chloride are evaporated under vacuum and water is added to the residue. The resultant aqueous mixture is extracted with ether and the ether extract washed with water, dried over magnesium sulfate and evaporated to dryness. The resulting residue is recrystallized from cyclohexane to yield 4-(4'-methoxybenzylthio)-acetophenone.

Similarly, replacing 4-methoxy benzyl chloride with other aralkyl halides or substituted aralkyl halides containing at least one substituent on the aryl moiety selected from the group consisting of halo, lower alkyl, lower alkoxy, trifluoromethyl, nitro and cyano is productive of the corresponding substituted aralkylthioacetophenones.

The starting compounds of Formula II are prepared from the above substituted aralkylthioacetophenones according to the procedure in U.S. Pat. No. 3,679,697.

PREPARATION B

A mixture of 2 g. of 4-methylthioacetophenone, 5 g. of acetic acid, and approximately 3.8 g. of 30% hydrogen peroxide is heated at 85° - 95° C. until an exothermic reaction is initiated. When the reaction subsides, .002 g. of palladium-on-carbon is introduced and the reaction mixture is filtered through diatomaceous earth. The filtrate is chilled to precipitate the product which is isolated by filtration and air dried to yield 4-methylsulfonyl acetophenone.

Similarly, replacing 4-methylthioacetophenone with other thioacetophenones, for example,
4-t-butylthioacetophenone,
4-benzylthioacetophenone,
4-(4'-chlorobenzylthio)acetophenone,
4-(4'-methoxybenzylthio)acetophenone,
4-phenylthioacetophenone, and
4-(4'-chlorophenylthio)acetophenone
is productive of the following sulfonyl substituted acetophenones:
4-t-butylsulfonylacetophenone,
4-benzylsulfonylacetophenone,
4-(4'-chlorobenzylsulfonyl)acetophenone,
4-(4'-methoxybenzylsulfonyl)acetophenone,
4-phenylsulfonylacetophenone, and
4-(4'-chlorophenylsulfonyl)acetophenone.

The starting compounds of Formula II are prepared from the above sulfonyl substituted acetophenones according to the procedure in U.S. Pat. No. 3,679,697.

EXAMPLE 1

A. A mixture of 1 g. of 1-(2,4,β-trichlorophenethyl) imidazole, 1.8 g. of 3,4-dichlorothiophenol and 1.5 g. of potassium carbonate in 50 ml. of acetone is stirred and refluxed for 4 hours. The solvent is evaporated under vacuum and 20 ml. of water is added to the residue. The resultant aqueous mixture is extracted with ether and the ether extract washed with 50 ml. of a saturated sodium chloride solution. The organic phase is dried over magnesium sulfate and evaporated to yield 1-[2,4-dichloro-β-(3',4'-dichlorophenylthio)phenethyl] imidazole.

The oxalate salt of the free base is prepared by the dropwise addition of ethereal oxalic acid to the free base in ether until precipitation is complete. The product is collected by filtration and recrystallized from a mixture of acetone and ethyl acetate to yield 1-[2,4-dichloro-β-(3',4'-dichlorophenylthio)phenethyl]-imidazole oxalate, M.P. 161.5°-163.5° C.

B. Similarly, substituting other starting materials of Formula II for 1-(2,4,β-trichlorophenethyl)imidazole, for example, 1-(β-chlorophenethyl)imidazole;
1-(β-chloro-4-ethylphenethyl)imidazole;
1-(β-chloro-4-t-butylphenethyl)imidazole;
1-(β-chloro-4-ethoxyphenethyl)imidazole;
1-(β-chloro-4-n-butoxyphenethyl)imidazole;
1-(β-chloro-4-t-butoxyphenethyl)imidazole;
1-(4,β-dichlorophenethyl)imidazole;
1-(3,4,β-trichlorophenethyl)imidazole;
1-(4-bromo-β-chlorophenethyl)imidazole;
1-(2,4-dibromo-β-chlorophenethyl)imidazole;
1-(β-chloro-4-fluorophenethyl)imidazole;
1-(β-chloro-2,4-difluorophenethyl)imidazole;
1-(β-chloro-2-trifluoromethylphenethyl)imidazole;
1-(β-chloro-4-trifluoromethylphenethyl)imidazole;
1-(β-chloro-4-cyanophenethyl)imidazole,
1-(β-chloro-4-nitrophenethyl)imidazole, and
1-(β-chloro-2-thiocyanophenethyl)imidazole is productive of the following 1-[β-(3',4'-dichlorophenylthio)phenethyl]imidazoles which, where indicated, are further characterized as the acid addition salts by treatment in the conventional manner with the appropriate acid:

1-[β-(3',4'-dichlorophenylthio)phenethyl]imidazole;
1-[4-ethyl-β-(3',4'-dichlorophenylthio)phenethyl]-imidazole;
1-[4-t-butyl-β-(3',4'-dichlorophenylthio)phenethyl]-imidazole, nitrate salt, decomp. 142.5°–146.5° C.
1-[4-ethoxy-β-(3',4'-dichlorophenylthio)phenethyl]-imidazole;
1-[4-n-butoxy-β-(3',4'-dichlorophenylthio)phenethyl]imidazole;
1-[4-t-butoxy-β-(3',4'-dichlorophenylthio)phenethyl]-imidazole;
1-[4-chloro-β-(3',4'-dichlorophenylthio)phenethyl]-imidazole;
1-[3,4-dichloro-β-(3',4'-dichlorophenylthio)phenethyl]imidazole, nitrate salt, decomp. 133°–137° C.;
1-[4-bromo-β-(3',4'-dichlorophenylthio)phenethyl]-imidazole;
1-[2,4-dibromo-β-(3',4'-dichlorophenylthio)phenethyl]imidazole, nitrate salt, decomp. 132.5°–134.5° C.;
1-[4-fluoro-β-(3',4'-dichlorophenylthio)phenethyl]-imidazole;
1-[2,4-difluoro-β-(3',4'-dichlorophenylthio)phenethyl]imidazole, oxalate salt, decomp. 172.5°–175° C.;
1-[2-trifluoromethyl-β-(3',4'-dichlorophenylthio)-phenethyl]imidazole; p1 1-[4-trifluoromethyl-β-(3',4'-dichlorophenylthio)phenethyl]imidazole;
1-[4-cyano-β-(3',4'-dichlorophenylthio)phenethyl]-imidazole;
1-[4-nitro-β-(3',4'-dichlorophenylthio)phenethyl]-imidazole, and
1-[2-thiocyano-β-(3',4'-dichlorophenylthio)phenethyl]imidazole.

C. In like manner, substituting other starting materials of Formula III for 3,4-dichlorothiophenol, for example, 4-chlorothiophenol and 2,4-dichlorothiophenol and using the above recited starting compounds of Formula II is productive of the following 1-[β-(R-thio)phenethyl]imidazoles which, where indicated are further characterized as the acid addition salts by treatment in the conventional manner with the appropriate acid:

1-[β-(4'-chlorophenylthio)phenethyl]imidazole, oxalate salt, decomp. 147.5°–149° C.;
1-[β-(2',4'-dichlorophenylthio)phenethyl]imidazole;
1-[4-ethyl-β-(4'-chlorophenylthio)phenethyl]-imidazole;
1-[4-ethyl-β-(2',4'-dichlorophenylthio)phenethyl]-imidazole;
1-[4-t-butyl-β-(4'-chlorophenylthio)phenethyl]-imidazole;
1-[4-t-butyl-β-(2',4'-dichlorophenylthio)phenethyl]-imidazole;
1-[4-ethoxy-β-(4'-chlorophenylthio)phenethyl]-imidazole;
1-[4-ethoxy-β-(2',4'-dichlorophenylthio)phenethyl]-imidazole
1-[4-n-butoxy-β-(4'-chlorophenylthio)phenethyl]-imidazole;
1-[4-n-butoxy-β-(2',4'-dichlorophenylthio)phenethyl]imidazole;
1-[4-t-butoxy-β-(4'-chlorphenylthio)phenethyl]-imidazole;
1-[4-t-butoxy-β-(2',4'-dichlorophenylthio)phenethyl]-imidazole;
1-[4-chloro-β-(4'-chlorophenylthio)phenethyl]-imidazole, oxalate salt, decomp. 190°–191° C.;
1-[4-chloro-β-(2',4'-dichlorophenylthio)phenethyl]-imidazole;
1-[2,4-dichloro-β-(4'-chlorophenylthio)phenethyl]-imidazole, nitrate salt, M.P. 169.5°–170° C.;
1-[2,4-dichloro-β-(2',4'-dichlorophenylthio)phenethyl]imidazole, nitrate salt, M.P. 150°–151° C.;
1-[3,4-dichloro-β-(4'-chlorophenylthio)phenethyl]-imidazole, nitrate salt, decomp. 123°–125.5° C.;
1-[3,4-dichloro-β-(2',4'-dichlorophenylthio)phenethyl]imidazole, oxalate salt, decomp. 169°–171.5° C.;
1-[4-bromo-β-(4'-chlorophenylthio)phenethyl]-imidazole;
1-[4-bromo-β-(2',4'-dichlorophenylthio)phenethyl]-imidazole;
1-[2,4-dibromo-β-(4'-chlorophenylthio)phenethyl]-imidazole;
1-[2,4-dibromo-β-(2',4'-dichlorophenylthio)phenethyl]imidazole;
1-[4-fluoro-β-(4'-chlorophenylthio)phenethyl]-imidazole;
1-[4-fluoro-β-(2',4'-dichlorophenylthio)phenethyl]-imidazole;
1-[2,4-difluoro-β-(4'-chlorophenylthio)phenethyl]-imidazole;
1-[2,4-difluoro-β-(2',4'-dichlorophenylthio)phenethyl]imidazole;
1-[2-trifluoromethyl-β-(4'-chlorophenylthio)phenethyl]imidazole;
1-[2-trifluoromethyl-β-(2',4'-dichlorophenylthio)-phenethyl]imidazole;
1-[4-trifluoromethyl-β-(4'-chlorophenylthio)phenethyl]imidazole;
1-[4-trifluoromethyl-β-(2',4'-dichlorophenylthio)-phenethyl]imidazole;
1-[4-cyano-β-(4'-chlorophenylthio)phenethyl]-imidazole;
1-[4-cyano-β-(2',4'-dichlorophenylthio)phenethyl]-imidazole;
1-[4-nitro-β-(4'-chlorophenylthio)phenethyl]-imidazole;
1-[4-nitro-β-(2',4'-dichlorophenylthio)phenethyl]-imidazole;

1-[2-thiocyano-β-(4'-chlorophenylthio)phenethyl]-
  imidazole; and
1-[2-thiocyano-β-(2',4'-dichlorophenylthio)phene-
  thyl]imidazole.

EXAMPLE 2

A. A solution of 1 g. of 1-(2,4,β-trichlorophenethyl-
)imidazole in 10 ml. of tetrahydrofuran is added to a
mixture of 1 g. of 2,4-dichlorobenylmercaptan and 220
mg. of 56% sodium hydride dispersion in 40 ml. of
tetrahydrofuran. After stirring for 12 hours at room
temperature, the solvent is evaporated under vacuum
and 10 ml. of water is added to the residue. The resul-
tant aqueous mixture is extracted with ether and the
ether extract washed with 50 ml. of a saturated sodium
chloride solution. The organic phase is dried over mag-
nesium sulfate the evaporated to yield 1-[2,4-dichloro-
β-(2',4'-dichlorobenzylthio)phenethyl]imidazole.

The nitrate salt of the free base is prepared by the
dropwise addition of nitric acid to the free base in ether
until precipitation is complete. The product is collected
by filtration and recrystallized from ethyl acetate to
yield 1-[2,4-dichloro-β-(2',4'-dichlorobenzylthio)phene-
thyl]imidazole nitrate, decomp. 133.5°-134.5° C.

B. Similarly, substituting other starting materials of
Formula II, i.e., those recited in paragraph B of Exam-
ple 1, is productive of the following 1-[β-(2',4'-
dichlorobenzylthio)phenethyl]imidazoles which, where
indicated, are further characterized as the acid addition
salts by treatment in the conventional manner with the
appropriate acid:

1-[β-(2',4'-dichlorobenzylthio)phenethyl]imidazole;
1-[4-ethyl-β-(2',4'-dichlorobenzylthio)phenethyl]-
  imidazole;
1-[4-t-butyl-β-(2',4'-dichlorobenzylthio)phenethyl]-
  imidazole;
1-[4-ethoxy-β-(2',4'-dichlorobenzylthio)phenethyl]-
  imidazole;
1-[4-n-butoxy-β-(2',4'-dichlorobenzylthio)phenethyl]-
  imidazole;
1-[4-t-butoxy-β-(2',4'-dichlorobenzylthio)phenethyl]-
  imidazole;
1-[4-chloro-β-(2',4'-dichlorobenzylthio)phenethyl]-
  imidazole;
1-[3,4-dichloro-β-(2',4'-dichlorobenzylthio)phene-
  thyl]imidazole, nitrate salt, decomp. 107°-110° C.;
1-[4-bromo-β-(2',4'-dichlorobenzylthio)phenethyl]-
  imidazole;
1-[2,4-dibromo-β-(2',4'-dichlorobenzylthio)phene-
  thyl]imidazole;
1-[4-fluoro-β-(2',4'-dichlorobenzylthio)phenethyl]-
  imidazole;
1-[2,4-difluoro-β-(2',4'-dichlorobenzylthio)phene-
  thyl]imidazole;
1-[2-trifluoromethyl-β-(2',4'-dichlorobenzylthio)-
  phenethyl]imidazole;
1-[4-trifluoromethyl-β-(2',4'-dichlorobenzylthio)-
  phenethyl]imidazole;
1-[4-cyano-β-(2',4'-dichlorobenzylthio)phenethyl]-
  imidazole;
1-[4-nitro-β-(2',4'-dichlorobenzylthio)phenethyl]-
  imidazole; and
1-[2-thiocyano-β-(2',4'-dichlorobenzylthio)phene-
  thyl]imidazole.

C. In like manner, substituting other starting materials
of Formula III for 2,4-dichlorobenzylmercaptan, for
example, 4-chlorobenzylmercaptan, 3,4-dichloroben-
zylmercaptan or heptylmercaptan and using the starting
materials of Formula II recited in paragraph B of Exam-
ple 1 is productive of the following 1-[β-(R-thio)phene-
thyl]imidazoles which, where indicated, are further
characterized as the acid addition salts by treatment in
the conventional manner with the appropriate acid:

1-[β-(4'-chlorobenzylthio)phenethyl]imidazole;
1-[β-(3',4'-dichlorobenzylthio)phenethyl]imidazole;
1-[β-(n-heptylthio)phenethyl]imidazole;
1-[4-ethyl-β-(4'-chlorobenzylthio)phenethyl]-
  imidazole;
1-[4-ethyl-β-(3',4'-dichlorobenzylthio)phenethyl]-
  imidazole;
1-[4-ethyl-β-(n-heptylthio)phenethyl]imidazole;
1-[4-t-butyl-β-(4'-chlorobenzylthio)phenethyl]-
  imidazole, oxalate salt, decomp. 156°-158.5° C.;
1-[4-t-butyl-β-(3',4'-dichlorobenzylthio)phenethyl]-
  imidazole;
1-[4-t-butyl-β-(n-heptylthio)phenethyl]imidazole;
1-[4-ethoxy-β-(4'-chlorobenzylthio)phenethyl]-
  imidazole;
1-[4-ethoxy-β-(3',4'-dichlorobenzylthio)phenethyl]-
  imidazole;
1-[4-ethoxy-β-(n-heptylthio)phenethyl]imidazole;
1-[4-n-butoxy-β-(4'-chlorobenzylthio)phenethyl]-
  imidazole, nitrate salt, decomp. 113°-114° C.;
1-[4-n-butoxy-β-(3',4'-dichlorobenzylthio)phenethyl]-
  imidazole;
1-[4-n-butoxy-β-(n-heptylthio)phenethyl]imidazole,
  oxalate salt, decomp. 124.5°-130° C.;
1-[4-t-butoxy-β-(4'-chlorobenzylthio)phenethyl]-
  imidazole;
1-[4-t-butoxy-β-(3',4'-dichlorobenzylthio)phenethyl]-
  imidazole;
1-[4-t-butoxy-β-(n-heptylthio)phenethyl]imidazole;
1-[4-chloro-β-(4'-chlorobenzylthio)phenethyl]-
  imidazole, oxalate salt, decomp. 148°-149.5° C.,
  nitrate salt, M.P. 103.5°-105.5° C.;
1-[4-chloro-β-(3',4'-dichlorobenzylthio)phenethyl]-
  imidazole;
1-[4-chloro-β-(n-heptylthio)phenethyl]imidazole;
1-[2,4-dichloro-β-(4'-chlorobenzylthio)phenethyl]-
  imidazole, nitrate salt, M.P. 130.5°-132° C.;
1-[2,4-dichloro-β-(3',4'-dichlorobenzylthio)phene-
  thyl]imidazole, nitrate salt, decomp. 95°-96.5° C.;
1-[2,4-dichloro-β-(n-heptylthio)phenethyl]imidazole,
  oxalate salt, M.P. 106°-109° C.;
1-[3,4-dichloro-β-(4'-chlorobenzylthio)phenethyl]-
  imidazole, oxalate salt, decomp. 174°-175° C.;
1-[3,4-dichloro-β-(3',4'-dichlorobenzylthio)phene-
  thyl]imidazole, oxalate salt, decomp. 176°-177.5°
  C.;
1-[3,4-dichloro-β-(n-heptylthio)phenethyl]imidazole;
1-[4-bromo-β-(4'-chlorobenzylthio)phenethyl]-
  imidazole;
1-[4-bromo-β-(3',4'-dichlorobenzylthio)phenethyl]-
  imidazole;
1-[4-bromo-β-(n-heptylthio)phenethyl]imidazole;
1-[2,4-dibromo-β-(4'-chlorobenzylthio)phenethyl]-
  imidazole, nitrate salt, decomp. 126.5°-128° C.;
1-[2,4-dibromo-β-(3',4'-dichlorobenzylthio)phene-
  thyl]imidazole;
1-[2,4-dibromo-β-(n-heptylthio)phenethyl]imidazole;
1-[4-fluoro-β-(4'-chlorobenzylthio)phenethyl]-
  imidazole;
1-[4-fluoro-β-(3',4'-dichlorobenzylthio)phenethyl]-
  imidazole;
1-[4-fluoro-β-(n-heptylthio)phenethyl]imidazole;

1-[2,4-difluoro-β-(4'-chlorobenzylthio)phenethyl]-
  imidazole;
1-[2,4-difluoro-β-(3',4'-dichlorobenzylthio)phene-
  thyl]imidazole, oxalate salt, decomp. 89.5°–93.5° C.;
1-[2,4-difluoro-β-(n-heptylthio)phenethyl]imidazole;
1-[2-trifluoromethyl-β-(4'-chlorobenzylthio)phene-
  thyl]imidazole;
1-[2-trifluoromethyl-β-(3', 4'-dichlorobenzylthio)-
  phenethyl]imidazole, nitrate salt, decomp.
  134.5°–137° C.;
1-[2-trifluoromethyl-β-(n-heptylthio)phenethyl]-
  imidazole;
1-[4-trifluoromethyl-β-(4'-chlorobenzylthio)phene-
  thyl]imidazole;
1-[4-trifluoromethyl-β-(3',4'-dichlorobenzylthio)-
  phenethyl]imidazole;
1-[4-trifluoromethyl-β-(n-heptylthio)phenethyl]-
  imidazole;
1-[4-cyano-β-(4'-chlorobenzylthio)phenethyl]-
  imidazole;
1-[4-cyano-β-(3',4'-dichlorobenzylthio)phenethyl]-
  imidazole;
1-[4-cyano-β-(n-heptylthio)phenethyl]imidazole;
1-[4-nitro-β-(4'-chlorobenzylthio)phenethyl]-
  imidazole;
1-[4-nitro-β-(3',4'-dichlorobenzylthio)phenethyl]-
  imidazole;
1-[4-nitro-β-(n-heptylthio)phenethyl]imidazole;
1-[2-thicyano-β-(4'-chlorobenzylthio)phenethyl]-
  imidazole;
1-[2-thiocyano-β-(3',4'-dichlorobenzylthio)phene-
  thyl]imidazole; and
1-[2-thiocyano-β-(n-heptylthio)phenethyl[imidazole.

EXAMPLE 3

Repeating the procedure recited in paragraph A of Example 1 using 1-(2,4,β-trichlorophenethyl)imidazole and 1-(3,4,β-trichlorophenethyl)imidazole as starting materials of Formula II and using 4-trifluoromethylthiophenol, 4-chloro3-trifluoromethylthiophenol, 3,4,5-trichlorothiophenol and pentachlorothiophenol as starting materials of Formula III is productive of the following 1-[β(R-thio)phenethyl]imidazoles which, where indicated, are further characterized as the acid addition salts by treatment in the conventional manner with the appropriate acid:

1-[2,4 -dichloro-β-(4'-trifluoromethylphenylthio)-
  phenethyl]imidazole, oxlate salt, decomp.
  178°–178.5° C.;
1-[2,4-dichloro-β-(4'-chloro-3'-trifluoromethylpheny-
  thio)phenethyl]imidazole, oxalate salt, decomp.
  186°–187.5° C.;
1-[2,4-dichloro-β-(3',4',5'-trichlorophenylthio)phene-
  thyl]imidazole, nitrate salt, decomp, 178°–185.5° C.;
1-[2,4-dichloro-β-(pentachlorophenylthio)phene-
  thyl]imidazole, nitrate salt, decomp. 201°–202.5° C.
1-[3,4-dichloro-β-(4'-trifluoromethylphenylthio)-
  phenethyl]imidazole, oxalate salt, decomp.
  170°–171° C.;
1-[3,4-dichloro-β-(4'-chloro-3'-trifluoromethyl-
  phenylthio)phenethyl]imidazole, oxalate salt, decomp. 165°–166° C.;
1-[3,4-dichloro-β-(3',4',5'-trichlorophenylthio)phene-
  thyl]imidazole; and
1-[3,4-dichloro-β-(pentachlorophenylthio)phene-
  thyl]imidazole.

EXAMPLE 4

Repeating the procedure recited in paragraph A of Example 2 but substituting other starting materials of Formula III for 2,4-dichlorobenzyl mercaptan, for example
ethyl mercaptan,
pentyl mercaptan,
octyl mercaptan,
nonyl mercaptan,
dodecyl mercaptan
octadecyl mercaptan,
3-phenylpropyl mercaptan,
cyclopentylpropyl mercaptan,
cyclohexyl mercaptan,
cyclohexylmethyl mercaptan,
cyclohexylethyl mercaptan,
cycloheptylmethyl mercaptan,
allyl mercaptan,
2-octenyl mercaptan,
3-phenyl-2-propenyl mercaptan,
3-(4-chlorophenyl)-2-propenyl mercaptan,
3-(4-fluorophenyl)-2-propenyl mercaptan,
3-hexynyl mercaptan,
2-octynyl mercaptan,
benzyl mercaptan,
4-methylbenzyl mercaptan,
4-t-butylbenzyl mercaptan,
4-trifluoromethylbenzyl mercaptan,
4-methoxybenzyl mercaptan,
3,4,5-trimethoxybenzyl mercaptan,
4-n-butoxybenzyl mercaptan,
2,4,5-trichlorobenzyl mercaptan,
4-bromobenzyl mercaptan,
4-fluorobenzyl mercaptan,
4-nitrobenzyl mercaptan, and
4-cyanobenzyl mercaptan,
is productive of the following 1-[2,4-dichloro-β-(R-thio)phenethyl[imidazoles which, where indicated, are further characterized as the acid addition salts by treatment in the conventional manner with the appropriate acid:

1-[2,4-dichloro-β-(ethylthio)phenethyl]imidazole;
1-[2,4-dichloro-β-(n-pentylthio)phenethyl]imidazole,
  oxalate salt, coalesces 99° C.;
1-[2,4-dichloro-β-(n-octylthio)phenethyl]imidazole,
  oxalate salt, M.P. 101.5°–103.5° C.;
1-[2,4-dichloro-β-(n-nonylthio)phenethyl]imidazole,
  oxalate salt, gels 82.5° C.;
1-[2,4-dichloro-β-(n-dodecylthio)phenethyl]-
  imidazole, oxalate salt, M.P. 124.5° C.;
1-[2,4-dichloro-β-(octadecylthio)phenethyl]-
  imidazole, oxalate salt, gels 91.5°–150° C.;
1-[2,4-dichloro-β-(3-phenylpropylthio)phenethyl]-
  imidazole, oxalate salt, M.P. 87.5°–90° C.;
1-[2,4-dichloro-β-(cyclopentylpropylthio)phenethyl]-
  imidazole;
1-[2,4-dichloro-β-(cyclohexylthio)phenethyl]-
  imidazole nitrate salt, M.P. 114.5°–117.5° C.;
1-[2,4-dichloro-β-(cyclohexylmethylthio)phenethyl]-
  imidazole, oxalate salt, decomp. 122.5°–140° C.;
1-[2,4-dichloro-β-(cyclohexylethylthio)pheneyl]-
  imidazole, oxalate salt, decomp. 104°–108.5° C;
1-[2,4-dichloro-β-(cycloheptylmethylthio)phene-
  thyl]imidazole;
1-[2,4-dichloro-β-(allythio)phenethyl]imidazole oxalate salt, M.P. 84.5°–123° C.;

1-[2,4-dichloro-β-(2-octenylthio)phenethyl]-
imidazole, oxalate salt, M.P. 112.5°-116.5° C.;

1-[2,4-dichloro-β-(3-phenyl-2-propenylthio)phene-
thyl]imidazole, oxalate salt, decomp. 151°-160.5°
C.;

1-{2,4-dichloro-β-[3-(4'-chlorophenyl)-2-propenyl-
thio]phenethyl}imidazole, nitrate salt, decomp.
123°-126° C.;

1-{2,4-dichloro-β-[3-(4'-fluorophenyl)-2-propenylthi-
o]phenethyl}imidazole,

1-[2,4-dichloro-β-(3-hexynylthio)phenethyl]-
imidazole, oxalate salt, M.P. 90.5°-95° C.;

1-[2,4-dichloro-β-(2-octynylthio)phenethyl]-
imidazole, oxalate salt, decomp. 118°-119.5° C.;

1-[2,4-dichloro-β-(benzylthio)phenethyl]imidazole;
nitrate salt, M.P. 110°-112° C.;

1-[2,4-dichloro-β-(4'-methylbenzylthio)phenethyl]-
imidazole, nitrate salt, M.P. 110.5°-112° C.;

1-[2,4-dichloro-β-(4'-t-butylbenzylthio)phenethyl]-
imidazole, nitrate salt, decomp. 162.5°-163° C.;

1-[2,4-dichloro-β-(4'-trifluoromethylbenzylthio)-
phenethyl]imidazole, nitrate salt, decomp.
112°-114° C.;

1-[2,4-dichloro-β-(4'-methoxybenzylthio)phenethyl]-
imidazole, nitrate salt, decomp. 118°-119.5° C.;

1-[2,4-dichloro-β-(3',4',5'-trimethoxybenzylthio)-
phenethyl]imidazole, oxalate salt, gels 147° C.;

1-[2,4-dichloro-β-(4'-n-butoxybenzylthio)phenethyl]-
imidazole, oxalate salt, decomp. 106.5°-108.5° C.;

1-[2,4-dichloro-β-(2',4',5'-trichlorobenzylthio)phene-
thyl]imidazole, nitrate salt, decomp. 172.5°-173.5°
C.;

1-[2,4-dichloro-β-(4'-bromobenzylthio)phenethyl]-
imidazole, nitrate salt, decomp. 137°-138° C.;

1-[2,4-dichloro-β-(4'-fluorobenzylthio)phenethyl]-
imidazole, nitrate salt, decomp. 104.5°-107.5° C.;

1-[2,4-dichloro-β-(4'-nitrobenzylthio)phenethyl]-
imidazole, nitrate salt, decomp. 129.5°-132° C.;

1-[2,4-dichloro-β-(4'-cyanobenzylthio)phenethyl]-
imidazole, nitrate salt, decomp. 119.5°-123° C.;

EXAMPLE 5

Repeating the procedure recited in paragraph A of Example 1 using 1-(4,β-dichlorophenylethyl)imidazole and 1-[2,4,β-trichlorophenethyl]imidazole as starting materials of Formula II and using other starting materials of Formula III for 3,4-dichlorothiophenol for example, thiophenol,
β-thioaphthol,
4-methylthiophenol,
4-methoxythiophenol,
3-methoxythiophenol,
2-chlorothiophenol,
3-chlorothiophenol,
2,5-dichlorothiophenol,
4-bromothiophenol,
4-fluorothiophenol,
4-nitrothiophenol,
4-aminothiophenol,
4-acetamidothiophenol, and
4-cyanothiophenol, is productive of the following 1-[4-chloro-β-(R-thio)-phenethyl]imidazoles and 1-[2,4-dichloro-β-(R-thio)-phenethyl]imidazole which, where indicated, are further characterized as the acid addition salts by treatment in the conventional manner with the appropriate acid:

1-[4-chloro-β-(phenylthio)phenethyl]imidazole, oxalate salt, decomp. 166°-167° C.;

1-[4-chloro-β-(2-napthylthio)phenethyl[imidazole, oxalate salt, M.P. 193.5°-194° C.;

1-[4-chloro-β-(4'-methylphenylthio)phenethyl]-
imidazole, oxalate salt, decomp. 199.5°-200° C.;

1-[4-chloro-β-(4'-methoxyphenylthio)phenethyl[-
imidazole, oxalate salt, decomp. 177°-178° C.;

1-[4-chloro-β-(3'-methoxyphenylthio)phenethyl]-
imidazole, oxalate salt, M.P. 164.5°-165.5° C.;

1-[4-chloro-β-(2'-chlorophenylthio)phenethyl]-
imidazole, oxalate salt, M.P. 177°-178° C.;

1-[4-chloro-β-(3'-chlorophenylthio)phenethyl]-
imidazole, oxalate salt, M.P. 169.5°-171.5° C.;

1-[4-chloro-β-(2',5'-dichlorophenylthio)phenethyl]-
imidazole, oxalate salt, M.P. 181.5°-183.5° C.;

1-[4-chloro-β-(4'-bromophenylthio)phenethyl]-
imidazole, oxalate salt, decomp. 185°-186.5° C.;

1-[4-chloro-β-(4'-fluorophenylthio)phenethyl]-
imidazole, oxalate salt, M.P. 182.5°-183° C.;

1-[4-chloro-β-(4'-nitrophenylthio)phenethyl]-
imidazole, oxalate salt, M.P. 203°-204.5° C.;

1-[4-chloro-β-(4'-aminophenylthio)phenethyl]-
imidazole;

1-[4-chloro-β-(4'-acetamidophenylthio)phenethyl]-
imidazole, oxalate salt, M.P. 149.5°-152° C.;

1-[4-chloro-β-(4'-cyanophenylthio)phenethyl]-
imidazole;

1-[2,4-dichloro-β-(phenylthio)phenethyl]imidazole;

1-[2,4-dichloro-β-(2-naphthylthio)phenethyl]-
imidazole;

1-[2,4-dichloro-β-(4'-methylphenylthio)phenethyl]-
imidazole;

1-[2,4-dichloro-β-(4'-methoxyphenylthio)phenethyl]-
imidazole;

1-[2,4-dichloro-β-(3'-methoxyphenylthio)phenethyl]-
imidazole;

1-[2,4-dichloro-β-(2'-chlorophenylthio)phenethyl]-
imidazole;

1-[2,4-dichloro-β-(3'-chlorophenylthio)phenethyl]-
imidazole;

1-[2,4-dichloro-β-(2',5'-dichlorophenylthio)phene-
thyl]imidazole;

1-[2,4-dichloro-β-(4'-bromophenylthio)phenethyl]-
imidazole;

1-[2,4-dichloro-β-(4'-fluorophenylthio)phenethyl]-
imidazole;

1-[2,4-dichloro-β-(4'-nitrophenylthio)phenethyl]-
imidazole;

1-[2,4-dichloro-β-(4'-aminophenylthio)phenethyl]-
imidazole;

1-[2,4-dichloro-β-(4'-acetamidophenylthio)phene-
thyl]imidazole; and

1-[2,4-dichloro-β-(4'-cyanophenylthio)phenethyl]-
imidazole.

EXAMPLE 6

To a solution of 400 mg. of 1-[4-chloro-β-(4'-aminophenylthio)phenethyl]imidazole oxalate in 20 ml. of tetrahydrofuran containing 1 ml. of triethylamine is added 0.5 ml. of hexanoyl chloride. After stirring for 30 minutes at room temperature, the solvent is evaporated under vacuum and aqueous potassium carbonate is added to the residue. The resultant aqueous mixture is extracted with dichloromethane and the organic phase is acidified with oxalic acid. The product which precipitates is filtered off and recrystallized from a mixture of acetone and ethyl acetate to yield 1-[4-chloro-β-(4'-hexanoylaminophenylthio)phenethyl]imidazole oxalate, M.P. 98.5°–102° C.

Similarly, substituting other acid chlorides for hexanoyl chloride, for example propionyl chloride, n-valeryl chloride, decanoyl chloride and the like is productive of the corresponding 1-[4-chloro-$\beta$-(4'-propionylaminophenylthio)phenethyl]imidazole oxalate;

1-[4-chloro-$\beta$-(4'-valeroylaminophenylthio)phenethyl]imidazole oxalate;

1-[4-chloro-$\beta$-(4'-decanoylaminophenylthio)phenethyl]imidazole oxalate, and so forth.

EXAMPLE 7

1-[4-chloro-$\beta$-(4'-chlorophenylthio)phenethyl]imidazole nitrate (1 g.) is treated with aqueous potassium carbonate until a pH of approximately 11 is obtained, whereupon the free base, i.e., 1-[4-chloro-$\beta$-(4'-chlorophenylthio)phenethyl]imidazole, which separates is extracted with dichloromethane. The extract is dried with magnesium sulfate and evaporated. To the resulting residue, in 50 ml. of chloroform at 0° C. is slowly added with stirring, a solution of 700 mg. of 85% m-chloroperbenzoic acid in 50 ml. of chloroform. When the addition is complete, stirring at 0° C. is continued for approximately 3 hours. Thereafter, the reaction mixture is washed with aqueous potassium carbonate and aqueous sodium chloride, dried over magnesium sulfate and evaporated. The residue is crystallized from benzene to yeild 1-[4-chloro-$\beta$-(4'-chlorophenylsulfinyl)phenethyl]imidazole, M.P. 139°–140° C, which is further characterized as the oxalate salt, M.P. 167°–167° C.

Similarly, repeating the above procedure on the 1-[$\beta$-(R-thio)phenethyl]imidazole salts obtained in Examples 1 thru 6 is productive of the corresponding 1-[$\beta$-(R-sulfinyl)phenethyl]imidazoles which can be further characterized by conversion in the usual manner to the indicated acid addition salts, e.g., 1-[2,4-dichloro-$\beta$-(n-dodecylsulfinyl)phenethyl]imidazole, oxalate salt, decomp. 134°–138° C.;

1-[4-chloro-$\beta$-(4'-chlorobenzylsulfinyl)phenethyl]imidazole, nitrate salt, decomp. 161.5°–162° C.;

1-[2,4-dichloro-$\beta$-(4'-chlorobenzylsulfunyl)phenethyl]imidazole, nitrate salt, M.P. 141°–142° C. (foaming);

1-[2,4-dichloro-$\beta$-(n-heptylsulfinyl)phenethyl]imidazole;

1-[2,4-dichloro-$\beta$-(2',4'-dichlorobenzylsulfinyl)phenethyl]imidazole;

1-[2,4-dichloro-$\beta$-(3',4'-dichlorophenylsulfinyl)phenethyl]imidazole and so forth.

EXAMPLE 8

1-[4-(chloro-$\beta$-(4'-chlorophenylthio)phenethyl]imidazole nitrate (1 g.) is treated with aqueous potassium carbonate until a pH of approximately 11 is obtained whereupon the free base, i.e. 1-[4chloro-$\beta$-(4'-chlorophenylthio)phenethyl]imidazole, which separates is extracted with dichloromethane. The extract is dried with magnesium sulfate and evaporated. To the resulting residue in 50 ml. of chloroform at room temperature is slowly added with stirring a solution of 1.7 g. of 85% m-chloroperbenzoic acid in 50 ml. of chloroform. When the addition is complete, stirring at room temperature is continued for approximately 24 hours. Thereafter, the reaction mixture is washed with aqueous potassium carbonate and aqueous sodium chloride, dried over magnesium sulfate and evaporated. The residue is crystallized from benzene to yield 1-[4-chloro-$\beta$-[4'-chlorophenylsulfonyl)phenethyl]imidazole, M.P. 176°–178.5° C.

Similarly, repeating the above procedure on the 1-[$\beta$-(R-thio)phenethyl]imidazoles or acid addition salts obtained in Examples 1 thru 6 is productive of the corresponding 1-[$\beta$-R-sulfonyl)-phenethyl]imidazoles which can be further characterized by conversion in the usual manner to the indicated acid addition salts, e.g., 1-[2,4-dichloro-$\beta$-(dodecylsulfonyl)phenethyl]imidazole, oxalate salt, decomp. 105.5°–110° C.;

1-[4-chloro-$\beta$-(4'-chlorobenzylsulfonyl)phenethyl]imidazole, nitrate salt, decomp. 181° C.; and so forth.

EXAMPLE 9

A solution of 85% m-chloroperbenzoic acid in chloroform (2 g/100 ml.) is added dropwise, over a period of one hour, to a stirred solution of 2.53 g. of 1-[$\beta$-chloro-4-methylthiophenethyl]imidazole in 150 ml. of chloroform at 0° C. After 6 hours, the resultant solution is washed with aqueous potassium carbonate and with water. The organic phase is separated and dried over magnesium sulfate. Evaporation of the solvent yields 1-[$\beta$-chloro-4-methylsulfinylphenethyl]imidazole.

Similarly, replacing 1-[$\beta$-chloro-4-methylthiophenethyl]imidazole with other 1-[$\beta$-chloro-R$^1$-thiophenethyl]imidazoles, for example, 1-[$\beta$-chloro-4-t-butylthiophenethyl]imidazole;

1-[$\beta$-chloro-4-benzylthiophenethyl]imidazole;

1-[$\beta$-chloro-4-(4'-chlorobenzylthio)phenethyl]imidazole;

1-[$\beta$-chloro-4-(4'-methoxybenzylthio)phenethyl]imidazole;

1-[$\beta$-chloro-4-phenylthiophenethyl]imidazole, and

1-[$\beta$-chloro-4-(4'-chlorophenylthio)phenethyl]imidazole, is productive of:

1-[$\beta$-chloro-4-t-butylsulfinylphenethyl]imidazole;

1-[$\beta$-chloro-4-benzylsulfinylphenethyl]imidazole;

1-[$\beta$-chloro-4-(4'-chlorobenzylsulfinyl)phenethyl]imidazole;

1-[$\beta$-chloro-4-(4'-methoxybenzylsulfinyl)phenethyl]imidazole;

1-[$\beta$-chloro-4-phenylsulfinylphenethyl]imidazole, and

1-[$\beta$-chloro-4-(4'-chlorophenylsulfinyl)phenethyl]imidazole.

EXAMPLE 10

Repeating the procedure recited in paragraph A of Example 1 using 3,4-dichlorothiophenol as the starting material of Formula III and using other starting materials of Formula II for 1-(2,4,$\beta$-trichlorophenethyl)imidazole, for example, 1-($\beta$-chloro-4-methylthiophenethyl)imidazole;

1-($\beta$-chloro-4-t-butylthiophenethyl)imidazole;

1-($\beta$-chloro-4-benzylthiophenethyl)imidazole;

1-[$\beta$-chloro-4-(4'-chlorobenzylthio)phenethyl]imidazole;

1-[$\beta$-chloro-4-(4'-methoxybenzylthio)phenethyl]imidazole;

1-($\beta$-chloro-4-phenylthiophenethyl)imidazole;

1-[$\beta$-chloro-4-(4'-chlorophenylthio)phenethyl]imidazole;

1-($\beta$-chloro-4-methylsulfinylphenethyl)imidazole;

1-($\beta$-chloro-4-t-butylsulfinylphenethyl)imidazole;

1-($\beta$-chloro-4-benzylsulfinylphenethyl)imidazole;

1-[β-chloro-4-(4'-chlorobenzylsulfinyl)phenethyl]-imidazole;
1-[β-chloro-4-(4'-methoxybenzylsulfinyl)phenethyl]-imidazole;
1-(β-chloro-4-phenylsulfinylphenethyl)imidazole;
1-[β-chloro-4-(4'-chlorophenylsulfinyl)phenethyl]-imidazole;
1-(β-chloro-4-methylsulfonylphenethyl)imidazole;
1-(β-chloro-4-t-butylsulfonylphenethyl)imidazole;
1-(β-chloro-4-benzylsulfonylphenethyl)imidazole;
1-[β-chloro-4-(4'-chlorobenzylsulfonyl)phenethyl]-imidazole;
1-[β-chloro-4-(4'-methoxybenzylsulfonyl)phenethyl]-imidazole;
1-[β-chloro-4-phenylsulfonylphenethyl]imidazole, and
1-[β-chloro-4-(4'-chlorophenylsulfonyl)phenethyl]-imidazole;

is productive of the following 1-[β-(3',4'-dichlorophenylthio)phenethyl]imidazoles:

1-(4-methylthio-β-(3',4'-dichlorophenylthio)phenethyl]imidazole, oxalate salt, decomp. 146°–148.5° C.;
1-[4-t-butylthio-β-(3',4'-dichlorophenylthio)phenethyl]imidazole;
1-[4-benzylthio-β-(3',4'-dichlorophenylthio)phenethyl]imidazole;
1-[4-(4-chlorobenzylthio)-β-(3',4'-dichlorophenylthio)phenethyl]imidazole;
1-[4-(4-methoxybenzylthio)-β-(3',4'-dichlorophenylthio)phenethyl]imidazole;
1-[4-phenylthio-β-(3',4'-dichlorophenylthio)phenethyl]imidazole;
1-[4-(4-chlorophenylthio)-β-(3',4'-dichlorophenylthio)phenethyl]imidazole;
1-[4-methylsulfinyl-β-(3',4'-dichlorophenylthio)-phenethyl]imidazole;
1-[4-t-butylsufinyl-β-(3',4'-dichlorophenylthio)phenethyl]imidazole;
1-[4-benzylsulfinyl-β-(3',4'-dichlorophenylthio)-phenethyl]imidazole;
1-[4-chlorobenzylsulfinyl)-β-(3',4'-dichlorophenylthio)phenethyl]imidazole;
1-[4-(4 -methoxybenzylsulfinyl)-β-(3',4'-dichlorophenylthio)phenethyl]imidazole;
1-[4-phenylsulfinyl-β-(3',4'-dichlorophenylthio)-phenethyl]imidazole;
1-[4-(4-chlorophenylsulfinyl)-β-(3',4'-dichlorophenylthio)phenethyl]imidazole;
1-[4-methylsulfonyl-β-(3',4'-dichlorophenylthio)-phenethyl]imidazole;
1-[4-t-butylsulfonyl-β-(3',4'-dichlorophenylthio)-phenethyl]imidazole;
1-[4-benzylsulfonyl-β-(3',4'-dichlorophenylthio)-phenethyl]imidazole;
1-[4-(4-chlorobenzylsulfonyl)-β-(3',4'-dichlorophenylthio)phenethyl]imidazole;
1-[4-(4-methoxybenxylsulfonyl)-β-(3',4'-dichlorophenylthio)phenethyl]imidazole;
1-[4-phenylsulfonyl-β-(3',4'-dichlorophenylthio)-phenethyl]imidazole; and
1-[4-(4-chlorophenylsulfonyl)-β-(3',4'-dichlorophenylthio)phenethyl]imidazole.

EXAMPLE 11

Repeating the procedure recited in paragraph A of Example 2 using 4-chlorobenzyl mercaptan as the starting material of Formula III and using other starting materials of Formula II for 1-(2,4,β-trichlorophenethyl)imidazole, i.e., those starting materials of Formula II recited in Example 10, is productive of the following 1-[β-(4'-chlorobenzylthio)phenethyl]imidazoles:

1-[4-methylthio-β-(4'-chlorobenzylthio)phenethyl]-imidazole;
1-[4-t-butylthio-β-(4'-chlorobenzylthio)phenethyl]-imidazole;
1-[4-benzylthio-β-(4'-chlorobenzylthio)phenethyl]-imidazole;
1-[4-(4-chlorobenzylthio)-β-(4'-chlorobenzylthio)-phenethyl]imidazole;
1-[4-(4-methoxybenzylthio)-β-(4'-chlorobenzylthio)-phenethyl]imidazole;
1-[4-phenylthio-β-(4'-chlorobenzylthio)phenethyl]-imidazole;
1-[4-(4-chlorophenylthio)-β-(4'-chlorobenzylthio)-phenethyl]imidazole;
1-[4-methylsulfinyl-β-(4'-chlorobenzylthio)phenethyl]imidazole;
1-[4-t-butylsulfinyl-β-(4'-chlorobenzylthio)phenethyl]imidazole;
1-[4-benzylsulfinyl-β-(4'-chlorobenzylthio)phenethyl]imidazole;
1-[4-(4-chlorobenzylsulfinyl)-β-(4'-chlorobenzylthio)phenethyl]imidazole;
1-[4-(4-methoxybenzylsulfinyl)-β-(4'-chlorobenzylthio)phenethyl]imidazole;
1-[4-phenylsulfinyl-β-(4'-chlorobenzylthio)phenethyl]imidazole;
1-[4-(4-chlorophenylsulfinyl)-β-(4'-chlorobenzylthio)phenethyl]imidazole;
1-[4-methylsulfonyl-β-(4'-chlorobenzylthio)phenethyl]imidazole;
1-[4-t-butylsulfonyl-β-(4'-chlorobenzylthio)phenethyl]imidazole;
1-[4-benzylsulfonyl-β-(4'-chlorobenzylthio)phenethyl]imidazole;
1-(4-(4-chlorobenzylsulfonyl)-β-(4'-chlorobenzylthio)phenethyl]imidazole;
1-[4-(4-methoxybenzylsulfonyl)-β-(4'-chlorobenzylthio)phenethyl]imidazole;
1-[4-phenylsulfonyl-β-(4'-chlorobenzylthio)phenethyl]imidazole; and
1-[4-(4-chlorophenylsulfonyl)-β-(4'-chlorobenzylthio)phenethyl]imidazole.

EXAMPLE 12

Repeating the procedure recited in Example 7 (using the appropriate quantity of m-chloroperbenzoic acid) on the products obtained in Examples 10 and 11 is productive of the following 1-[β-(R-sulfinyl)phenethyl]-imidazoles;

1-[4-phenylthio-β-(3',4'-dichlorophenylsulfinyl)-phenethyl]imidazole;
1-[4-(4-chlorophenylthio)-β-(3',4'-dichlorophenylsulfinyl)phenethyl]imidazole;
1-[4-methylsulfinyl-β-(3',4'-dichlorophenylsulfinyl)-phenethyl]imidazole;
1-[4-t-butylsulfinyl-β-(3',4'-dichlorophenylsulfinyl)-phenethyl]imidazole;
1-[4-benzylsulfinyl-β-(3',4'-dichlorophenylsulfinyl)-phenethyl]imidazole;
1-[4-(4-chlorobenzylsulfinyl)-β-(3',4'-dichlorophenylsulfinyl)phenethyl]imidazole;
1-[4-(4-methoxybenzylsulfinyl)-β-(3',4'-dichlorophenylsulfinyl)phenethyl]imidazole;

1-[4-phenylsulfinyl-β-(3',4'-dichlorophenylsulfinyl)-phenethyl]imidazole;
1-[4-(4-chlorophenylsulfinyl)-β-(3',4'-dichlorophenylsulfinyl)phenethyl]imidazole;
1-[4-methylsulfonyl-β-(3',4'-dichlorophenylsulfinyl)-phenethyl]imidazole;
1-[4-t-butylsulfonyl-β-(3',4'-dichlorophenylsulfinyl)-phenethyl]imidazole;
1-[4-benzylsulfonyl-β-(3',4'-dichlorophenylsulfinyl)-phenethyl]imidazole;
1-[4-(4-chlorobenzylsulfonyl)-β-(3',4'-dichlorophenylsulfinyl)phenethyl]imidazole;
1-[4-(4-methoxybenzylsulfonyl)-β-(3',4'-dichlorophenylsulfinyl)phenethyl]imidazole;
1-[4-phenylsulfonyl-β-(3',4'-dichlorophenylsulfinyl)-phenethyl]imidazole;
1-[4-(4-chlorophenylsulfonyl-β-(3',4'-dichlorophenylsulfinyl)phenethyl]imidazole;
1-[4-phenylthio-β-(4'-chlorobenzylsulfinyl)phenethyl]imidazole;
1-[4-(4-chlorophenylthio)-β-(4'-chlorobenzylsulfinyl)phenethyl]imidazole;
1-[4-methylsulfinyl-β-(4'-chlorobenzylsulfinyl)phenethyl]imidazole;
1-[4-t-butylsulfinyl-β-(4'-chlorobenzylsulfinyl)phenethyl]imidazole;
1-[4-benzylsulfinyl-β-(4'-chlorobenzylsulfinyl)phenethyl]imidazole;
1-[4-(4-chlorobenzylsulfinyl)-β-(4'-chlorobenzylsulfinyl)phenethyl]imidazole;
1-[4-(4-methoxybenzylsulfinyl)-β-(4'-chlorobenzylsulfinyl)phenethyl]imidazole;
1-[4-phenylsulfinyl-β-(4'-chlorobenzylsulfinyl)phenethyl]imidazole;
1-[4-(4-chlorophenylsulfinyl)-β-(4'-chlorobenzylsulfinyl)phenethyl]imidazole;
1-[4-methylsulfonyl-β-(4'-chlorobenzylsulfinyl)-phenethyl]imidazole;
1-[4-t-butylsulfonyl-β-(4'-chlorobenzylsulfinyl)-phenethyl]imidazole;
1-[4-benzylsulfonyl-β-(4'-chlorobenzylsulfinyl)-phenethyl]imidazole;
1-[4-(4-chlorobenzylsulfonyl)-β-(4'-chlorobenzylsulfinyl)phenethyl]imidazole; and
1-[4-(4-methoxybenzylsulfonyl)-β-(4'-chlorobenzylsulfinyl)phenethyl]imidazole.

EXAMPLE 13

Repeating the procedure recited in Example 8 on the products obtained in Examples 10 and 11 is productive of the following 1-[β-(R-sulfonyl)phenethyl]imidazoles:
1-[4-phenylthio-β-(3',4'-dichlorophenylsulfonyl)-phenethyl]imidazole;
1-[4-(4-chlorophenylthio)-β-(3',4'-dichlorophenylsulfonyl)phenethyl]imidazole;
1-[4-phenylsulfinyl-β-(3',4'-dichlorophenylsulfonyl)-phenethyl]imidazole;
1-[4-(4-chlorophenylsulfinyl)-β-(3',4'-dichlorophenylsulfonyl)phenethyl]imidazole;
1-[4-methylsulfonyl-β-(3',4'-dichlorophenylsulfonyl)-phenethyl]imidazole;
1-[4-t-butylsulfonyl-β-(3',4'-dichlorophenylsulfonyl)-phenethyl]imidazole;
1-[4-benzylsulfonyl-β-(3',4'-dichlorophenylsulfonyl)-phenethyl]imidazole;
1-[4-(4-chlorobenzylsulfonyl)-β-(3',4'-dichlorophenylsulfonyl)phenethyl]imidazole;
1-[4-(4-methoxybenzylsulfonyl)-β-(3',4'-dichlorophenylsulfonyl)phenethyl]imidazole;
1-[4-phenylsulfonyl-β-(3',4'dichlorophenylsulfonyl)-phenethyl]imidazole;
1-[4-(4-chlorophenylsulfonyl)-β-(3',4'-dichlorophenylsulfonyl)phenethyl]imidazole;
1-[4-phenylthio-β-(4'-chlorobenzylsulfonyl)phenethyl]imidazole;
1-[4-(4-chlorophenylthio)-β-(4'-chlorobenzylsulfonyl)phenethyl]imidazole;
1-[4-phenylsulfinyl-β-(4'-chlorobenzylsulfonyl)-phenethyl]imidazole;
1-[4-(4-chlorophenylsulfinyl)-β-(4'-chlorobenzylsulfonyl)phenethyl]imidazole;
1-[4-methylsulfonyl-β-(4'-chlorobenzylsulfonyl)-phenethyl]imidazole;
1-[4-t-butylsulfonyl-β-(4'-chlorobenzulsulfonyl)-phenethyl]imidazole;
1-[4-benzylsulfonyl-β-(4'-chlorobenzylsulfonyl)-phenethyl]imidazole;
1-[4-(4-chlorobenzylsulfonyl)-β-(4'-chlorobenzylsulfonyl)phenethyl]imidazole;
1-[4-(4-methoxybenzylsulfonyl)-β-(4'-chlorobenzylsulfonyl)phenethyl]imidazole;
1-[4-phenylsulfonyl-β-(4'-chlorobenzylsulfonyl)-phenethyl]imidazole; and
1-[4-(4-chlorophenylsulfonyl)-β-(4'-chlorobenzylsulfonyl)phenethyl]imidazole.

EXAMPLE 14

Repeating the procedure recited in Example 1, using reactants as dictated by the particular 1-[β-(R-thio)-phenethyl]imidazole desired, is productive of the following compounds which, where indicated, are further characterized as the acid addition salts by treatment in the conventional manner with the appropriate acid.
1-[2,4-dichloro-β-(4'-nitro-3'-trifluoromethylphenylthio)phenethyl]imidazole, nitrate salt, decomp. 127.5°–130.5°C.;
1-[4-trifluoromethyl-β-(4'-tert-butylphenylthio)-phenethyl]imidazole, oxalate salt, M.P. 161°–162° C.;
1-[2,4-dimethyl-β-(3',4'-dichlorophenylthio)phenethyl]imidazole, nitrate salt, decomp. 165.5°–166° C.;
1-[4-methoxy-β-(3',4'-dichlorophenylthio)phenethyl]imidazole, oxalate salt, M.P. 145.5° C.;
1-[4-methoxy-β-(4'-tert-butylphenylthio)phenethyl]-imidazole, oxalate salt, M.P. 139.5°–141.4° C.;
1-[2,4-dimethoxy-β-(3',4'-dichlorophenylthio)phenethyl]imidazole, nitrate salt, decomp. 155.5°–158° C.;
1-[4-nitro-β-(pentachlorophenylthio)phenethyl]-imidazole, nitrate salt, decomp. 163.5°–165.5° C;
1-[2,4-dichloro-β-(n-butoxyphenylthio)phenethyl]-imidazole, oxalate salt, M.P. 143°–144° C.;
1-[4-cyano-β-(pentachlorophenylthio)phenethyl]-imidazole, nitrate salt, M.P. 182.5° C. (foaming);
1-[4-n-butylthio-β-(4'-chlorophenylthio)phenethyl]-imidazole, oxalate salt, decomp. 159°–162° C.;
1-[4-(2',4'-dichlorobenzylthio)-β-(4'-fluorophenylthio)phenethyl]imidazole, oxalate salt, decomp. 99°–101° C.

EXAMPLE 15

Repeating the procedure recited in Example 2, using reactants as dictated by the particular 1-[β-(R-thio)-phenethyl]imidazole desired, is productive of the following compounds which, where indicated, are further characterized as the acid addition salts by treatment in the conventional manner with the appropriate acid:

1-[2,4-difluoro-β-(n-nonylthio)phenethyl]imidazole, oxalate salt, M.P. 79.5°-84° C.;

1-[2,4-dimethyl-β-(4'-chlorobenzylthio)phenethyl]-imidazole, oxalate salt, decomp. 80.5°-83° C.;

1-[4-methoxy-β-(3-phenylpropylthio)phenethyl]-imidazole, oxalate salt, M.P. 75°-83° C;

1-[4-methoxy-β-(n-dodecylthio)phenethyl]imidazole; oxalate salt, M.P. 90°-93° C.;

1-[2,4-dichloro-β-(1'-naphthylmethylthio)phenethyl]-imidazole, oxalate salt, coalesces 86° C., foams 86°-121.5° C.;

1-[4-chloro-β-(ethylthio)phenethyl]imidazole, oxalate salt, M.P. 157°-158° C.;

1-[2,4-dichloro-β-(n-undec-10-enylthio)phenethyl]-imidazole, oxalate salt, M.P. 82°-107° C.;

1-{2,4dichloro-β-[3-(4'-methylphenyl)prop-2-enylthio]phenethyl}imidazole, nitrate salt, M.P. 133.5°-137° C.;

1-{2,4-dichloro-β-[3-(4'tert-butylphenyl)prop-2-enylthio]phenethyl}imidazole, nitrate salt, M.P. 147°-153.5° C.;

1-[2,4-dichloro-β-(4-phenylbut-3-enylthio)phenethyl]imidazole;

1-{2,4-dichloro-β-[3-(4'-chlorophenyl)propylthio]-phenethyl}imidazole, oxalate salt, M.P. 111°-113° C.; 1-[2,4-dichloro-β-(prop-2-ynylthio)phenethyl]imidazole;

1-[4methylthio-β-(3',4'-dichlorobenzylthio)phenethyl]imidazole;

1-[4-n-butylthio-β-(4'-chlorobenzylthio)phenethyl]-imidazole, nitrate salt, decomp. 122°-124° C.;

1-[2,4-dichloro-β-(n-hexylthio)phenethyl]imidazole, oxalate salt, M.P. 110.5°-112° C.;

1-[2,4-dichloro-β-(n-propylthio)phenethyl]imidazole, nitrate salt, M.P. 101°-102.5° C.;

1-[2,4-dichloro-β-(n-butylthio)phenethyl]imidazole;

1-[2,4-dibromo-β-(n-pentylthio)phenethyl]imidazole;

1-[2,4-dibromo-β-(n-hexylthio)phenethyl]imidazole;

1-[2,4-dibromo-β-(n-octylthio)phenethyl]imidazole;

1-[2,4-difluoro-β-(n-octylthio)phenethyl]imidazole;

1-[2,4-difluoro-β-(n-decylthio)phenethyl]imidazole; and

1-[4-(2',4'-dichlorobenzylthio)-β-(ethylthio)phenethyl]imidazole, oxalate salt, decomp. 123°-126° C.

EXAMPLE 16

1-[4-chloro-β-(4'-chlorophenylthio)phenethyl]-imidazole nitrate (1 g.) in 100 ml. of dichloromethane is shaken with excess dilute potassium carbonate solution until the salt is completely dissolved. The organic layer is then separated, washed with water and dried over magnesium sulfate. Evaporation of the solvent yields 1-[4-chloro-β-(4'-chlorophenylthio)phenethyl]-imidazole as a gum.

In similar manner, the antimicrobial acid addition salts of all compounds of Formula (I) can be converted to the corresponding compounds in base form, for example:

1-[2,4-dichloro-β-(3',4'-dichlorophenylthio)phenethyl]imidazole;

1-[2,4-dichloro-β-(2',4'-dichlorobenzylthio)phenethyl]imidazole;

1-[2,4-dichloro-β-(n-heptylthio)phenethyl]imidazole;

1-[2,4-dichloro-β-(4'-chlorophenylthio)phenethyl]-imidazole.

1-[2,4-dichloro-β-(4'-chlorobenzylthio)phenethyl]-imidazole, and so forth.

EXAMPLE 17

Nitric acid (70%; d=1.42) is added dropwise to a stirred solution of 2.5 g. of 1-[4-chloro-β-(4'chlorophenylthio)phenethyl]imidazole in 40 ml. anhydrous ether until precipitation is complete. The product is filtered off, washed with ether and dried. Recrystallization from ethyl acetate yields 1-[4-chloro-β-(4'-chlorophenylthio)phenethyl]imidazole nitrate, M.P. 136.5°-137.5° C..

In similar manner, all compounds of Formula (I) in base form can be converted to the antimicrobial acid addition salts by treatment in the conventional manner with the appropriate acid.

EXAMPLE 18

This example demonstrates the preparation of the optical isomers of 1-[2,4-dichloro-β-(4'-chlorobenzylthio)phenethyl]-imidazole nitrate.

Distilled thionyl chloride (0.5 ml.) is added dropwise to a solution of 0.27 g. of (+)-1-(2,4-dichloro-β-hydroxyphenethyl)-imidazole[$\alpha_D^{25}$=+99° (c=1, methanol), see U.S. Pat. No. 3,839,574] in 50 ml. of dichloromethane at 0° C. After stirring for 2 hours, the solvent is removed in vacuo. The resultant residue, a pale yellow gum, is dissolved in 50 ml. of dichloromethane, and the solution neutralized with dilute potassium carbonate solution, dried over magnesium sulfate and evaporated to yield 0.29 g. of 1-(2,4-dichloro-β-chlorophenethyl)imidazole.

The above obtained 1-(2,4-dichloro-β-chlorophenethyl)-imidazole is dissolved in 10 ml. of dry tetrahydrofuran and added dropwise and with rapid stirring under nitrogen to a suspension of the salt prepared from 0.47 g. of 4-chlorobenzylthiol and 0.08 g. of sodium hydride (57% dispersion in mineral oil) in 25 ml. of dry tetrahydrofuran. The mixture is stirred overnight at room temperature under nitrogen. The solvent is then removed and 5 ml. of a saturated sodium chloride solution is added to the residue. The resultant aqueous mixture is extracted with ether and the combined extracts dried over magnesium sulfate and acidified with nitric acid. The product which precipitates is filtered off and recrystallized from ethyl acetate to yield (+)-1-[2,4-dichloro-β-(4-chlorobenzylthio)phenethyl]imidazole nitrate, M.P. 132.5°-134° C.(foaming) $\alpha_D^{25}$=+101.8° (c=1,methanol).

Similarly, replacing (+)-1-(2,4-dichloro-β-hydroxyphenyl)-imidazole with (−)-1(2,4-dichloro-β-hydroxyphenyl)imidazole [$\alpha_D^{25}$=−97.1°(c=1, methanol), see U.S. Pat. No. 3,839,547) the above procedure yields (−)-1-[2,4-dichloro-β-(4-chlorobenzylthio)phenethyl]-imidazole nitrate, M.P. 136°-137.5° C.(foaming); $\alpha_D^{25}$=−103.5° (c=1 methanol).

In like manner, substituting other thiols for 4-chlorobenzylthiol in the above procedure yields the optical isomers of the corresponding 1-[2,4-dichloro-β-(R-thio)phenethyl] imidazole salt. Moreover, replacing (+)-1-(2,4-dichloro-β-hydroxyphenethyl)imidazole with other suitable optically active alcohols yields other optically active compounds of Formula (I).

EXAMPLE 19

The following example illustrates the preparation of representative formulations containing an active compound, such as a salt of 1-[2,4-dichloro-β-(4'-chlorobenzylthio)phenethyl]imidazole, which may be used for control of fungi, bacteria and protozoa.

A. Topical Formulation

| | grams |
|---|---|
| Active compound | 0.2 - 2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA(butylated hydroxy anisole) | 0.01 |
| Water   qs | 100 |

All of the above ingredients, except water, are combined and heated at 60° C. with stirring. A sufficient quantity of water at 60° C. is then added with vigorous stirring to provide 100 g. of the cream formulation which is then cooled to room temperature.

B. I.V. Formulation

| | |
|---|---|
| Active compound | 0.5 g. |
| Propylene glycol | 20 g. |
| Polyethylene glycol 400 | 20 g. |
| Tween 80 | 1 g. |
| 0.9% Saline solution qs | 100 ml. |

The active compound is dissolved in propylene glycol, polyethylene glycol 400 and Tween 80. A sufficient quantity of 0.9% saline solution is then added with stirring to provide 100 ml. of the I.V. solution which is filtered through a 0.2 micron membrane filter and packaged under sterile conditions.

C. Oral Formulation

| | parts by weight |
|---|---|
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

What is claimed is:
1. A compound of the formula:

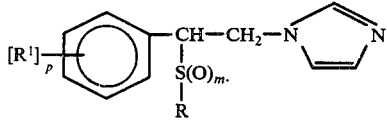

(I)

and the antimicrobial acid addition salts thereof, wherein:
R is alkyl, alkenyl, aralkenyl, substituted aralkenyl, alkynyl, cycloalkyl, cycloalkyl alkyl, aralkyl, substituted aralkyl, aryl or substituted aryl, said substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino alkanoylamino and cyano;

$R^1$ is hydrogen, halo, lower alkyl, lower alkoxy, trifluoromethyl, nitro, cyano, thiocyano or the group

in which $R^2$ is alkyl, cycloalkyl, aralkyl, substituted aralkyl, aryl or substituted aryl, and substituted aralkyl and said substituted aryl containing at least one substituent on the aryl moiety selected from the group consisting of halo, lower alkyl, lower alkoxy, trifluoromethyl, nitro and cyano;

and wherein with reference to the above, alkyl has 1 to 20 carbon atoms, cycloalkyl has 5 to 8 carbon atoms, cycloalkyl has 6 to 11 carbon atoms, alkenyl and alkynyl have 2 to 12 carbon atoms, aryl has 6 to 10 carbon atoms, aralkyl has 7 to 14 carbon atoms, aralkenyl has 8 to 14 carbon atoms, lower alkyl and lower alkoxy have 1 to 6 carbon atoms and alkanoylamino has 2 to 12 carbon atoms;

m, n and p are independently selected from the integers zero, 1 and 2;

provided that the value of m cannot be greater than the value of n except when $R^1$ is the group

and $R^2$ is aryl or substituted aryl.

2. The compound of claim 1 which is 1-[2,4-dichloro-β-(4'-chlorobenzylsulfinyl)phenethyl]imidazole and the antimicrobial acid addition salts thereof.

3. The compound of claim 1 which is 1-[2,4-dichloro-β-(n-heptylsulfinyl)phenethyl]imidazole and the antimicrobial acid addition salts thereof.

4. The compound of claim 1 which is 1-[2,4-dichloro-β-(2',4'-dichlorobenzylsulfinyl)phenethyl]imidazole and the antimicrobial acid addition salts thereof.

5. The compound of claim 1 which is 1-[2,4-dichloro-β-(3',4'-dichlorophenylsulfinyl)phenethyl]imidazole and the antimicrobial acid addition salts thereof.

6. A compound of claim 1 wherein m is zero.

7. A compound of claim 6 wherein $R^1$ is halo and R is alkyl, alkenyl, aralkenyl, halo substituted aralkenyl, aralkyl, halo or lower alkoxy substituted aralkyl, aryl or halo or lower alkoxy substituted aryl.

8. A compound of claim 7 wherein R is alkyl containing 1 to 12 carbon atoms, 2-alkenyl, 3-phenyl-2-alkenyl, halo substituted 3-phenyl-2alkenyl, benzyl, halo or lower alkoxy substituted benzyl, phenyl or halo or lower alkoxy substituted phenyl.

9. A compound of claim 8 wherein $[R^1]_p$ is 2,4-dihalo.

10. The compound of claim 9 which is 1-[2,4-dichloro-β-(2-octenylthio)phenethyl]imidazole and the antimicrobial acid addition salts thereof.

11. The compound of claim 9 which is 1-[2,4-dichloro-β-(3-phenyl-2-propenylthio)phenethyl]imidazole and the antimicrobial acid addition salts thereof.

12. The compound of claim 9 which is 1-{2,4-dichloro-β-[3-(4'-chlorophenyl)-2- propenylthio]phenethyl}imidazole and the antimicrobial acid addition salts thereof.

13. The compound of claim 9 which is 1-{2,4-dichloro-β-[3-(4'-fluorophenyl)-2-propenylthio]phenethyl}imidazole and the antimicrobial acid addition salts thereof.

14. A compound of claim 9 wherein R is alkyl containing 4 to 10 carbon atoms, halo or methoxy substituted benzyl, or halo or methoxy substituted phenyl.

15. The compound of claim 14 which 1-[2,4-dibromo-β-(n-pentylthio)phenethyl]imidazole and the antimicrobial acid addition salts thereof.

16. The compound of claim 14 which is 1-[2,4-dibromo-β-(n-hexylthio)phenethyl]imidazole and the antimicrobial acid addition salts thereof.

17. The compound of claim 14 which is 1-[2,4-dibromo-β-(n-heptylthio)phenethyl]imidazole and the antimicrobial acid addition salts thereof.

18. The compound of claim 14 which is 1-[2,4-dibromo-β-(4'-chlorobenzylthio)phenethyl]imidazole and the antimicrobial acid addition salts thereof.

19. The compound of claim 14 which is 1-[2,4-dibromo-β-(3',4'-dichlorophenylthio)phenethyl]-imidazole and the antimicrobial acid addition salts thereof.

20. The compound of claim 14 which is 1-[2,4-dichloro-β-(4'-fluorobenzylthio)phenethyl]imidazole and the antimicrobial acid addition salts thereof.

21. The compound of claim 14 which is 1-[2,4-dichloro-β-(4'-methoxybenzylthio)phenethyl]imidazole and the antimicrobial acid addition salts thereof.

22. The compound of claim 14 which is 1-[2,4-dichloro-β-(4'-methoxyphenylthio)phenethyl]-imidazole and the antimicrobial acid addition salts thereof.

23. The compound of claim 14 which is 1-[2,4-difluoro-β-(n-heptylthio)phenethyl]imidazole and the antimicrobial acid addition salts thereof.

24. The compound of claim 14 which is 1-[2,4-difluoro-β-(n-octylthio)phenethyl]imidazole and the antimicrobial acid addition salts thereof.

25. The compound of claim 14 which is 1-[2,4-difluoro-β-(n-nonylthio)phenethyl]imidazole and the antimicrobial acid addition salts thereof.

26. A compound of claim 14 wherein [R¹]$_p$ is 2,4-dichloro and R is a straight chain alkyl containing 4 to 10 carbon atoms, chloro substituted benzyl or chloro substituted phenyl.

27. The compound of claim 26 which is 1-[2,4-dichloro-β-(n-butylthio)phenethyl]imidazole and the antimicrobial acid addition salts thereof.

28. The compound of claim 26 which is 1-[2,4-dichloro-β-(n-octylthio)phenethyl]imidazole and the antimicrobial acid addition salts thereof.

29. The compound of claim 26 which is 1-[2,4-dichloro-β-(n-nonylthio)phenethyl]imidazole and the antimicrobial acid addition salts thereof.

30. The compound of claim 26 which is 1-[2,4-dichloro-β-(3',4',5'-trichlorophenylthio)phenethyl]-imidazole and the antimicrobial acid addition salts thereof.

31. A compound of claim 26 wherein R is a straight chain alkyl containing 5 to 7 carbon atoms, 4-chloro-, 2,4-dichloro- or 3,4-dichlorobenzyl, or 4-chloro-, 2,4-dichloro- or 3,4-dichlorophenyl.

32. The compound of claim 31 which is 1-[2,4-dichloro-β-(n-pentylthio)phenethyl]imidazole and the antimicrobial acid addition salts thereof.

33. The compound of claim 31 which is 1-[2,4-dichloro-β-(n-hexylthio)phenethyl]imidazole and the antimicrobial acid addition salts thereof.

34. The compound of claim 31 which is 1-[2,4-dichloro-β-(n-heptylthio)phenethyl]imidazole and the antimicrobial acid addition salts thereof.

35. The compound of claim 31 which is 1-[2,4-dichloro-β-(4'-chlorobenzylthio)phenethyl]imidazole and the antimicrobial acid addition salts thereof.

36. The compound of claim 31 which is 1-[2,4-dichloro-β-(2',40'-dichlorobenzylthio)phenethyl]-imidazole and the antimicrobial acid addition salts thereof.

37. The compound of claim 31 which is 1-[2,4-dichloro-β-(3',4'-dichlorobenzylthio)phenethyl]-imidazole and the antimicrobial acid addition salts thereof.

38. The compound of claim 31 which is 1-[2,4-dichloro-β-(4'-chlorophenylthio)phenethyl]imidazole and the antimicrobial acid addition salts thereof.

39. The compound of claim 31 which is 1-[2,4-dichloro-β-(2',4'-dichlorophenylthio)phenethyl]-imidazole and the antimicrobial acid addition salts thereof.

40. The compound of claim 31 which is 1-[2,4-dichloro-β-(3',4'-dichlorophenylthio)phenethyl]-imidazole and the antimicrobial acid addition salts thereof.

41. A composition useful for inhibiting the growth of fungi, bacteria or protozoa which comprises an effective amount of a compound of the formula:

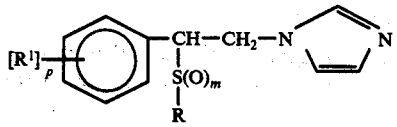

(I)

or an antimicrobial acid addition salt thereof, wherein:
R is alkyl, alkenyl, aralkenyl, substituted aralkenyl, alkynyl, cycloalkyl, cycloalkyl alkyl, aralkyl, substituted aralkyl, aryl and substituted aryl, said substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino, alkanoylamino and cyano;
R¹ is hydrogen, halo, lower alkyl, lower alkoxy, trifluoromethyl, nitro, cyano, thiocyano and the group

in which R² is alkyl, cycloalkyl, aralkyl, substituted aralkyl, aryl and substituted aryl, said substituted aralkyl and said substituted aryl containing at least one substituent on the aryl moiety selected from the group consisting of halo, lower alkyl, lower alkoxy, trifluoromethyl, nitro and cyano;
and wherein with reference to the above, alkyl has 1 to 20 carbon atoms, cycloalkyl has 5 to 8 carbon atoms, cycloalkyl alkyl has 6 to 11 carbon atoms, alkenyl and alkynyl have 2 to 12 carbon atoms, aryl has 6 to 10 carbon atoms, aralkyl has 7 to 14 carbon atoms, aralkenyl has 8 to 14 carbon atoms, lower alkyl and lower alkoxy have 1 to 6 carbon atoms and alkanoylamino has 2 to 12 carbon atoms;

m, n and p are independently selected from the integers zero, 1 and 2;

provided that the value of m cannot be greater than the value of n except when R¹ is the group

and R² is aryl or substituted aryl; in admixture with a suitable carrier.

42. A composition of claim 41 for pharmaceutical use wherein the carrier is a pharmaceutically acceptable, non-toxic carrier.

43. A composition of claim 42 for topical administration wherein the compound of Formula (I) is present in an amount ranging between 0.1 and 10.0 weight percent of the composition.

44. A method of inhibiting the growth of fungi, bacteria or protozoa which comprises applying to a host object containing, or subject to attack by fungi, bacteria or protozoa, an effective amount of a compound of the formula

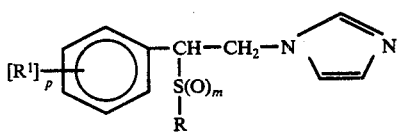
(I)

or an antimicrobial acid addition salt thereof or a composition containing same as an active ingredient, wherein:

R is alkyl, alkenyl, aralkenyl, substituted aralkenyl, alkynyl cycloalkyl, cycloalkyl alkyl, aralkyl, substituted aralkyl, aryl or substituted aryl, said substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino alkanoylamino and cyano;

R¹ is hydrogen, halo, lower alkyl, lower alkoxy, trifluoromethyl, nitro, cyano, thiocyano or the group

in which R² is alkyl, cycloalkyl, aralkyl, substituted aralkyl, aryl or substituted aryl, said substituted aralkyl and said substituted aryl containing at least one substituent on the aryl moiety selected from the group consisting of halo, lower alkyl, lower alkoxy, trifluoromethyl, nitro and cyano;

and wherein with reference to the above, alkyl has 1 to 20 carbon atoms, cycloalkyl has 5 to 8 carbon atoms, cycloalkyl alkyl has 6 to 11 carbon atoms, alkenyl and alkynyl have 2 to 12 carbon atoms, aralkyl has 7 to 14 carbon atoms, aralkenyl has 8 to 14 carbon atoms, lower alkyl and alkoxy have 1 to 6 carbon atoms and alkanoylamino has 2 to 12 carbon atoms;

m, n and p are independently selected from the integers zero, 1 and 2;

provided that the value of m cannot be greater than the value of n except when R¹ is the group

and R² is aryl or substituted aryl.

45. The method of claim 44 wherein the compound of Formula (I) is administered topically.

46. The method of claim 44 wherein the compound of Formula (I) is administered orally or parenterally.

* * * * *

UNITED STATES PATENT OFFICE
CERTIFICATE OF CORRECTION

Patent No. 4,055,652　　　　　　　　　Dated October 25, 1977

Inventor(s) Keith A. M. Walker

It is certified that error appears in the above-identified patent and that said Letters Patent are hereby corrected as shown below:

The term of this patent subsequent to August 30, 1994 has been disclaimed.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*

UNITED STATES PATENT AND TRADEMARK OFFICE

CERTIFICATE EXTENDING PATENT TERM
UNDER 35 U.S.C. 156

Patent No.    : 4,055,652

Dated         : Oct. 25, 1977

Inventor(s)   : Keith A.M. Walker

Patent Owner  : Syntex(U.S.A.) Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this Third day of September 1986.

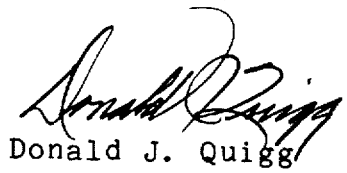

Donald J. Quigg

Assistant Secretary and Commissioner of Patents and Trademarks